United States Patent [19]

Chum et al.

[11] Patent Number: 4,476,025
[45] Date of Patent: Oct. 9, 1984

[54] SEPARATION OF CERTAIN CARBOXYLIC ACIDS UTILIZING CATION EXCHANGE MEMBRANES

[75] Inventors: Helena L. Chum, Arvada, Colo.; David W. Sopher, Maarssenbroek, Netherlands

[73] Assignee: The United States of America as represented by the United States Department of Energy, Washington, D.C.

[21] Appl. No.: 492,925

[22] Filed: May 9, 1983

[51] Int. Cl.³ .............................................. B01D 13/00
[52] U.S. Cl. .................................... 210/638; 210/500.2
[58] Field of Search ...................... 210/639, 638, 321.1, 210/500.2

[56] References Cited

U.S. PATENT DOCUMENTS 4,075,093  2/1978  Walch et al. ........................ 210/639

Primary Examiner—Frank Spear
Attorney, Agent, or Firm—Kenneth L. Richardson; James W. Weinberger; Michael F. Esposito

[57] ABSTRACT

A method of substantially separating monofunctional lower carboxylic acids from a liquid mixture containing the acids wherein the pH of the mixture is adjusted to a value in the range of from about 1 to about 5 to form protonated acids. The mixture is heated to an elevated temperature not greater than about 100° C. and brought in contact with one side of a perfluorinated cation exchange membrane having sulfonate or carboxylate groups or mixtures thereof with the mixture containing the protonated acids. A pressure gradient can be established across the membrane with the mixture being under higher pressure, so that protonated monofunctional lower carboxylic acids pass through the membrane at a substantially faster rate than the remainder of the mixture thereby substantially separating the acids from the mixture.

19 Claims, 2 Drawing Figures

SEPARATION OF CERTAIN CARBOXYLIC ACIDS UTILIZING CATION EXCHANGE MEMBRANES

CONTRACTUAL ORIGIN OF THE INVENTION

The invention described herein was made in the course of, or under, a contract with the U.S. Department of Energy.

BACKGROUND OF THE INVENTION

During the last decade there has been considerable interest in the electrochemical field in use of cation exchange membranes as separators in electrochemical cells particularly in the industrial chlor-alkali field and in redox batteries. The cation exchange membranes are perfluorinated and non-fluorinated ionomer membranes containing sulfonate and/or carboxylic groups in the resin, the perfluorinated species being discussed in an article entitled "ELECTROLYTIC CELL MEMBRANE DEVELOPMENT SURGES" by Stinson in the Mar. 15, 1982 issue of the C & E News, the disclosure of which is incorporated herein by reference. These materials are permeable to cations but provide an effective barrier to anions and are particularly attractive in the electrochemical battery field because they are highly conducting, highly selective in the materials which they pass and have suitable mechanical properties. An additional important characteristic in the electrochemical cells is that these membranes are chemically and thermally stable at cell operating conditions.

SUMMARY OF THE INVENTION

We have discovered that the cation exchange membranes similar to those previously used in the production of caustic and in batteries and electrochemical cells are useful in separating monofunctional lower carboxylic acids from mixtures containing said acids.

Accordingly, it is a principal object of the present invention to provide a method of substantially separating monofunctional lower carboxylic acids from a liquid mixture containing the acids comprising contacting one side of a cation exchange membrane with the mixture while maintaining the pH of the mixture acid, whereby the monofunctional lower carboxylic acids pass through the membrane at a substantially faster rate than the remainder of the mixture thereby substantially separating the monofunctional lower carboxylic acids from the mixture.

Another object of the present invention is to provide a method of substantially separating monofunctional lower carboxylic acids from a liquid mixture containing the acids comprising forming protonated monofunctional lower carboxylic acids, contacting one side of a cation exchange membrane with the mixture having the protonated monofunctional lower carboxylic acids, whereby the protonated monofunctional lower carboxylic acids pass through the membrane at a substantially faster rate than the remainder of the mixture thereby substantially separating the monofunctional lower carboxylic acids from the mixture.

Yet another object of the present invention is to provide a method of substantially separating monofunctional lower carboxylic acids from a liquid mixture containing the acids comprising forming protonated acids by adjusting the pH of the mixture, heating the mixture to a temperature in excess of ambient temperature, contacting one side of a cation exchange membrane with the heated mixture having the monofunctional protonated lower carboxylic acids, whereby the protonated monofunctional lower carboxylic acids pass through the membrane at substantially faster rate than the remainder of the mixture thereby substantially separating the protonated monofunctional lower carboxylic acids from the mixture.

A final object of the present invention is to provide a method of substantially separating monofunctional lower carboxylic acids from a liquid mixture containing the acids comprising adjusting the pH of the mixture to a value in the range of from about 1 to about 5 to form protonated acids, heating the mixture to an elevated temperature not greater than about 80° C., contacting one side of a perfluorinated cation exchange membrane having sulfonate and/or carboxylate groups with the mixture containing the protonated acids, establishing a pressure gradient across the membrane with the mixture being under higher pressure, whereby the protonated monofunctional lower carboxylic acids pass through the membrane at a substantially faster rate than the remainder of the mixture thereby substantially separating the acids from the mixture.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DETAILED DESCRIPTION OF THE INVENTION

During our study of the electrochemical reduction of levulinic acid in a cell having a lead cathode and a cation exchange membrane of the type previously discussed produced by DuPont under the trade name Nafion type 125, unreinforced or reinforced, it was anticipated that the membrane would be impervious to both the starting material as well as the valeric acid reduction product but that the membrane would allow the protons formed in the anode compartment to the migrate to the cathode compartment where they would maintain a low pH. Contrary to our expectations, it was surprisingly discovered that in fact after electrolysis most of the valeric acid reaction product formed in the cathode compartment was found in the anode compartment along with a small amount of the levulinic acid. Additional materials were tested in the test device illustrated in FIG. 1 to establish the efficacy of the method to separate monofunctional lower carboxylic acids from liquid mixtures containing the acid.

Figure 1:
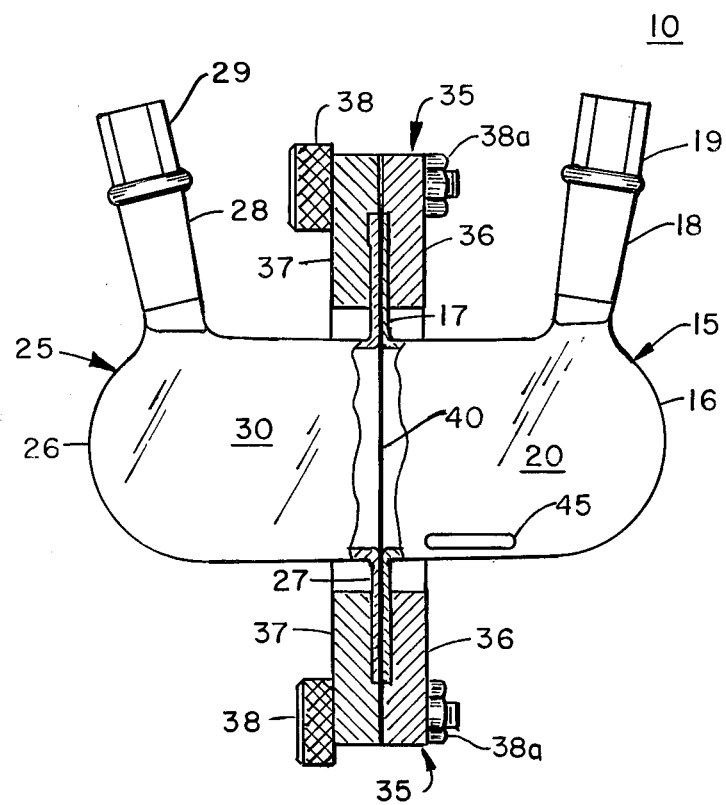
FIG. 1 is an elevational view partly in section of a diffusion cell useful for practicing the method of the present invention.
Figure 2:
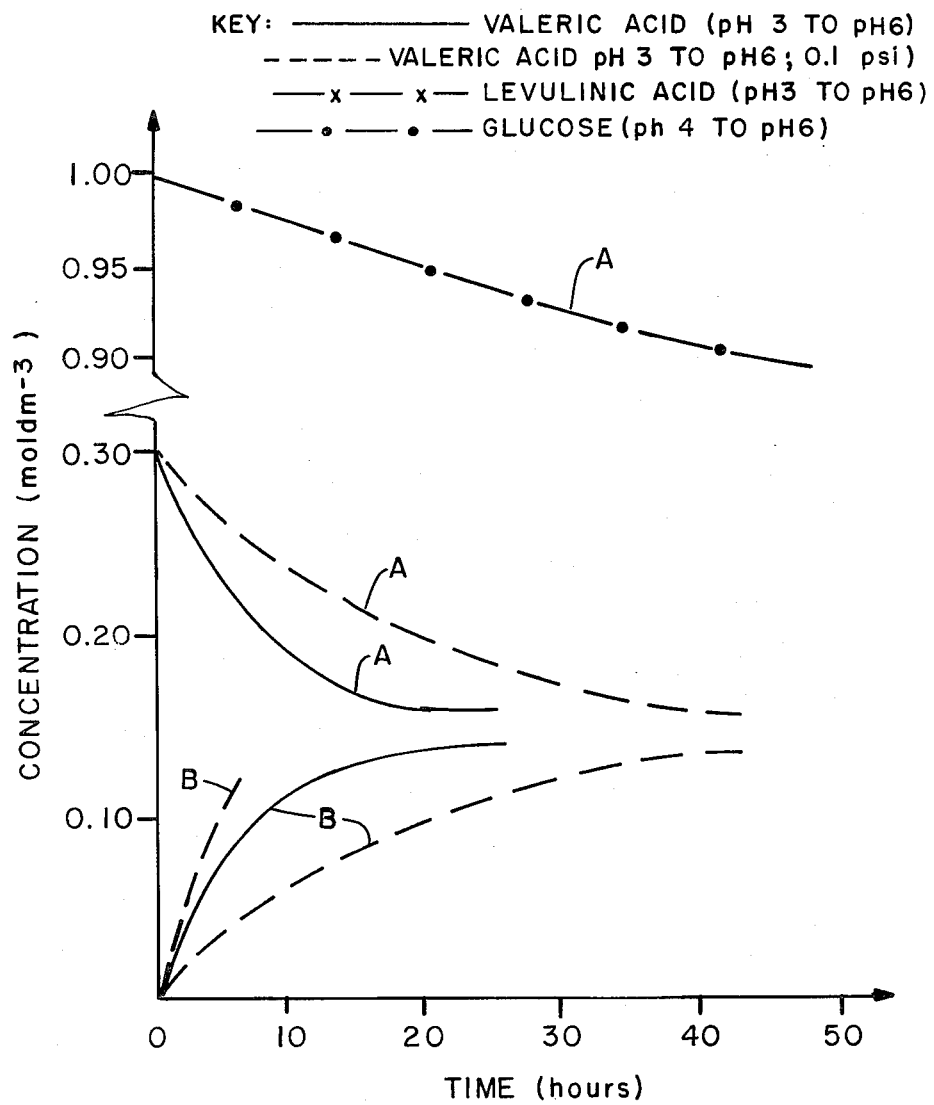
FIG. 2 is a graphical illustration of the relationship between time and concentration for various carboxylic acids in a mixture in contact with a cation exchange membrane, at room temperature, with the A curves representing concentrations of compounds in the compartment from which diffusion was occurring and with the B curves representing concentrations of compounds in the compartment to which diffusion was occurring.

Referring to FIG. 1 the cell 10 consists of two half cells 15 and 25, the half cell 15 having a generally tubular housing 16 with a circular flange 17 at one end thereof. A feed tube 18 enters the half cell 15 at the end thereof away from the flange 17 and is provided with a stopper 19 for hermetically sealing the half cell which forms the chamber 20. The other half cell 25 is also constructed of a similarly shaped tubular housing 26 having a circular flange 27 at one end thereof and a feed tube 28 at the other end thereof provided with a stopper 29 for hermetically sealing same. The half cell 25 forms a chamber 30 of the same size and dimension as the chamber 20.

Two half cells 15, 25 are joined together by a pair of locking mechanisms 35 each of which is provided with two apertured fittings 36, 37 and tightening bolts 38 and nuts 38a adapted to clamp the fittings together and to maintain same in clamped relation. The fittings 36, 37 contact the outsides of the flanges 17, 27 respectively of half cells 15, 25 between which is positioned a cation exchange membrane 40 of the type discussed. Finally, a magnetic stirbar 45 is located in the chamber 20 of the half cell 15.

In the following examples the half cells 15, 25 were made of glass and each half cell had a volume of 30 cm$^3$. The fittings 36, 37 were Teflon collars bolted together in a well-known manner. The membrane material was Nafion, although Flemion produced by the Asahi Glass Company is a suitable alternative. Other similar cation exchange membranes may also be suitable. In each case, the membrane 40 was removed after the example and prior to the next test, the new membrane material 40 was pretreated by boiling in deionized water for about 20 minutes after which it was wiped dry and clamped in the two half cells 15, 25. In each case one of the half cells such as 15 was filled with the solution containing the compound whose migration was being examined and the other half cell such as 25 was filled with water or a buffer solution. At various time intervals, samples were removed from each side of the cell 10 by the appropriate feed tube 18, 28 and analyzed by either uv spectroscopy or gas chromatography. Only the compartment 20 from which the diffusion was occurring was stirred continuously by the magnetic stirbar 45 but the materials in the other compartment 30 were thoroughly mixed before taking each sample. Pressure was increased on the material from which the diffusion was taking place by attaching a burette (not shown) to the feed tube 18 in the half cell 15 and filling the burette to a height of about 60 cm with the same solution as in the half cell.

Initial use of the cell 10 was to recreate the conditions present in the electrolysis cell. A valeric acid solution having a pH of less than about 2 at a concentration of 0.3 moles per liter was introduced into compartment 20 of half cell 15. The membrane 40 was Nafion and diffusion through the membrane 40 occurred rapidly so that after 20 hours the concentrations in compartments 20 and 30 were the same. Additional examples of valeric acid were performed wherein the pH was varied in the range of from about 1 to about 9 with the effective range for substantial diffusion of the valeric acid from one compartment to the other being in the range of from about 1 to 5 with the preferred pH range being in the range of from about 1 to about 3, see Table 1.

TABLE 1

Diffusion of valeric acid through "Nafion"-125; expressed as % acid diffused in 20 hours (% D, 20 h) initial diffusion rate (I.D.R., in moldm$^{-3}$h$^{-1}$), geometric area of the membrane:

| Conditions | % D,20 h | I.D.R. |
|---|---|---|
| Valeric acid (0.3 M) in H$_2$SO$_4$ (1 M) to H$_2$SO$_4$ (1 M) | 50 | 0.015 |
| Valeric acid (0.3 M) in water to water | 50 | 0.015 |
| Valeric acid (0.3 M) in pH 6 buffer to pH 6 buffer | 10 | 0.015 |
| Valeric acid (0.3 M) in pH 6 buffer to pH 9 buffer | 15 | 0.002 |
| Valeric acid (0.3 M) in water at pH 4 to water | 40 | 0.011 |
| Valeric acid (0.1 M) in water to water | 40 | 0.003 |
| Valeric acid (0.3 M) in water to water with 0.1 psi pressure drop across membrane | — | 0.019 |

As reported in Table 1 above, a 0.3 molar valeric solution in a 1.0 molar sulfuric acid solution diffused into a 1.0 molar sulfuric acid solution at a rate such that after 20 hours the concentrations in compartments 20 and 30 were identical. It was found that the initial diffusion rate for the valeric acid transferring from compartment 20 to compartment 30 was 0.015 moles per liter per hour at room temperature.

The above example was repeated using a a 0.3 molar valeric acid solution in water in compartment 20 and a water solution in compartment 30. The initial diffusion rate was the same and after 20 hours the percent diffusion or concentration in compartments 20 and 30 was the same as previously reported.

A 0.3 molar valeric acid solution buffered to a pH of 6 in compartment 20 was tested with a solution in compartment 30 buffered to a pH of 6. As seen from Table 1, the percent of valeric diffused from compartment 20 to 30 after 20 hours was only 10% and the initial diffusion rate was one-tenth of that reported for the lower pHs.

Establishing a pH gradient across the Nafion membrane 40 resulted in some improved results. A 0.3 molar valeric acid solution buffered to a pH of 6 was introduced into compartment 20 and a solution without valeric acid was buffered to a pH of 9 was introduced into compartment 30. After 20 hours, only 15% of the valeric acid diffused from compartment 20 to 30 with the initial diffusion rate being 0.002 moles per liter per hour. The pH gradient across the membrane clearly improved both the rate of diffusion over 20 hours as well as improving the initial diffusion rate to some extent; however, it is clear that a pH of 6 in the chamber from which the carboxylic acid diffuses is too high to ensure adequate results.

A 0.3 molar valeric acid solution in water buffered to a pH of 4 was introduced into compartment 20 and water was introduced into compartment 30 as reported in Table 1. The percent of valeric acid diffused in 20 hours was 40% and the initial diffusion rate was 0.011 moles per liter per hour. From this example it is seen that a pH of 4 is sufficiently acidic to establish acceptable initial diffusion rates as well as acceptable separation values after 20 hours, although not as good as pHs in the preferred range of from about 1 to about 3. A 0.1 molar valeric acid solution diffusing into water provided good separation but poor initial diffusion rates.

Finally, a 0.3 molar valeric acid in water solution was introduced into compartment 20 and water was introduced in compartment 30. By the aforesaid method of introducing a burette tube into feeder tube 18, a 0.1 psi pressure drop was established across the membrane 40 with the initial diffusion rates being reported in Table 1 as 0.019 moles per liter per hour, an improvement over the previously reported initial diffusion rates, even at preferred conditions. Increasing the temperature increases the diffusion rate significantly for low activation energies are characteristic of the diffusion of low molecular weight carboxylic acids.

Additional examples were performed with two other monofunctional lower molecular weight aliphatic carboxylic acids, these being propionic and butyric acids both of which were found to migrate through the membrane 40 at essentially the same rates as valeric acid, see Table 2 and FIG. 3, thereby indicating that the diffusion rate is related to chemical functionality rather than molecular weight.

TABLE 2

Diffusion of organic compounds through "Nation"-125; expressed as % of compound diffused in 20 hours (% D, 20h) and initial diffusion rate (I.D.R.; moldm$^{-3}$h$^{-1}$) at different compound initial concentrations.

| COMPOUND | INITIAL CONC. (moldm$^{-3}$) 0.1 DIFFUSION | | INITIAL CONC. (moldm$^{-3}$) 0.3 DIFFUSION | | INITIAL CONCN. (moldm$^{-3}$) 1.0 DIFFUSION | |
|---|---|---|---|---|---|---|
| | % D, 20h | I.D.R. | % D, 20h | I.D.R. | % D, 20h | I.D.R. |
| Propionic acid[a] | 40 | 0.003 | — | — | — | — |
| Butyric acid[a] | 40 | 0.003 | — | — | — | — |
| Valeric acid[a] | 40 | 0.003 | — | — | — | — |
| Valeric acid | — | — | 50 | 0.015 | — | — |
| Valeric acid[b] | — | — | — | 0.019 | — | — |
| Levulinic acid | — | — | 30 | 0.0065 | — | — |
| Succinic acid | — | — | 25 | 0.0040 | — | — |
| Lactic acid | — | — | 25 | 0.0030 | — | — |
| Glucose | — | — | — | — | 5 | 0.006 |

[a]Acids all present in one solution, also containing 0.1 moldm$^{-3}$
[b]~0.1 p.s.i. drop in pressure across membrane It was found that substituted carboxylic acids with the polyfunctional groups such as levulinic acid, lactic acid, and succinic acid were all found to diffuse at substantially slower rates than the monofunctional lower carboxylic acids, see Table 2. By lower monofunctional carboxylic acids, it is meant carboxylic acids having 1 to 5 carbon atoms with a single functional group, that being the acid group. Polyfunctional carboxylic acids include the aforementioned lactic acid, succinic acid, levulinic acid as well as other acids such as fumaric acid, cinnamic acid and glutaric acid.

It is believed that maintaining the pH in the compartment from which the monofunctional lower carboxylic acid diffuses in the range of from about 1 to about 5 causes protonation of the carboxylic acid by interaction with hydroxonium acid forming a species illustrated below, the species having an overall positive charge which allows its migration through the cation exchange membrane:

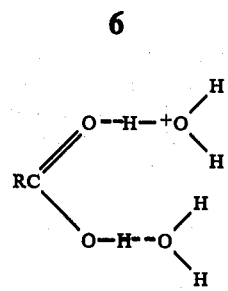

It is believed but not known for certain that polyfunctional carboxylic acids do not migrate through the membrane 40 at the same rate as the monofunctional lower carboxylic acids because of a possible interaction between the second or third functional group and the carboxylate and/or sulfonate groups in the membrane matrix which tends to retard the motion of the ion through the material.

Glucose is representative of cellulose, cellobiose, carbohydrates including polysaccharides, starch, inulin, cellulose, hemicellulose, and lignin do not diffuse through the membrane at any significant rate, again see Table 2. Table 2 illustrates that while the initial diffusion rate for glucose is as great as or greater than the reported polyfunctional carboxylic acids, the percent of material diffused after 20 hours is very small, probably due to the size of the molecule. Note also that the initial concentration of glucose is 3.3 times higher than that of any of the carboxylic acids tested.

As reported in Table 2, providing a pressure gradient across the membrane 90 as low as 0.1 psi results in a 40% increase in the rate of diffusion of a monofunctional lower carboxylic acid through the cation exchange membrane. These membranes can withstand pressures up to about 150 psi, whereby pressure gradients in the range of from about 0.1 to about 150 psi are useful. Similarly, it was found that an increase in temperature of the material in the compartment from which diffusion occurs is helpful since the activation energy for diffusion is low. It is important that the temperature of the mixture containing the monofunctional lower carboxylic acid is below the boiling point of the solution. It is also preferred that the temperature of the mixture in the compartment from which diffusion occurs be greater than ambient temperature but less than about 100° C.

The method of the present invention is useful in the soap industry wherein it is often desired to separate lower carboxylic acids from higher carboxylic acids, the higher carboxylic acids such as steric acid, oleic acid, palmitic acid, and the like are useful in the production of soap, whereas the lower carboxylic acids are not.

The method of the present invention is also useful in the biomass industries in general. For example, acid degradation of cellulose leads to levulinic acid and formic acid. The method of the present invention provides a way to separate the acids from cellulose and by-products of the acid degradation reaction.

Another major use for the subject invention is in the separation of lower carboxylic acids from mixtures produced in the processing of terrestrial or aquatic biomass, e.g., glucose fermenting to carboxylic acids (for instance, to butyric acid, valeric acid, lactic acid, or propionic acid, mixtures thereof). The microorganisms in the fermentation processes are inhibited as the medium decreases in pH as the result of production of carboxylic acid. By the method of the present invention, it is possible to remove the low molecular weight carboxylic acids from the desired fermentation liquid mixture as formed, and thereby prevent poisoning of the fermentation culture.

While there has been presented what at present is considered to be the preferred embodiments of the present invention, it will be understood that various modifications and alterations may be made therein without departing from the true scope and spirit of the present invention and it is intended to cover within the claims appended hereto all such modifications and alterations.

The embodiments of the invention in which an exclusive property or privilege is claimed are defined as follows:

1. A method of substantially separating monofunctional lower carboxylic acids consisting essentially of from 1 to 5 carbon atoms from a liquid mixture containing said acids, said method comprising the steps of:
   (a) contacting one side of a perfluorinated ionomer membrane;
   (b) maintaining a pH of said mixture acid; and
   (c) establishing a pressure gradient across said membrane of less than about 5 psi, whereby said monofunctional lower carboxylic acids pass through said membrane at a substantially faster rate than a remainder of said mixture thereby substantially separating said monofunctional lower carboxylic acids from said mixture.

2. A method of claim 1, wherein said perfluorinated ionomer membrane is a cation exchange membrane which contains carboxylate or sulfonate groups or mixtures thereof.

3. The method of claim 1, wherein said mixture has a pH in the range of from about 1 to about 5.

4. The method of claim 1, wherein said mixture has a pH in the range of from about 1 to about 3.

5. The method of claim 1, wherein said mixture contains polyfunctional lower carboxylic acids.

6. The method of claim 1, wherein said mixture contains high molecular weight carboxylic acids having more than five carbon atoms.

7. The method of claim 1, wherein said mixture contains a carbohydrate.

8. The method of claim 1, wherein said mixture contains a member from the group consisting of polysaccharides, simple saccharides, and oligomers thereof.

9. The method of claim 1, wherein said mixture contains a cellulose, a hemicellulose, or lignin.

10. The method of claim 1, wherein said mixture comprises a glucose fermentation, and said acid separated therefrom is selected from a group consisting of formic acid, propionic acid, butyric acid, valeric acid, and lactic acid.

11. The method of claim 1, wherein said mixture comprises a cheese whey fermentation and said acid separated therefrom is lactic acid.

12. A method of substantially separating monofunctional lower carboxylic acids consisting essentially of from 1 to 5 carbon atoms from a liquid mixture containing said acids, said process comprising the steps of;
   (a) adjusting a pH of the mixture to a value less than about 5;
   (b) contacting one side of a perfluorinated ionomer membrane with said mixture; and
   (c) establishing a pressure gradient across said membrane of less than about 5 psi, whereby said monofunctional lower carboxylic acids pass through said membrane at a substantially faster rate than a remainder of said mixture thereby substantially separating said acids from said mixture.

13. The method of claim 12, wherein the pH of the mixture is not greater than about 3.

14. The method of claim 12, wherein the pH of the mixture is in the range of about 1 to about 3.

15. The method of claim 12, wherein the pressure gradient across said membrane is around about 0.1 psi.

16. A method of substantially separating monofunctional lower carboxylic acids consisting of from 1 to 5 carbon atoms from a liquid mixture containing said acids, said process comprising the steps of:
   (a) contacting one side of a perfluorinated ionomer membrane with a mixture having protonated monofunctional lower carboxylic acids therein; and
   (b) establishing a pressure gradient across said membrane of less than about 5 psi, whereby said protonated monofunctional lower carboxylic acids pass through said membrane at a substantially faster rate than a remainder of said mixture thereby substantially separating said monofunctional lower carboxylic acids from said mixture.

17. The method of claim 16, wherein the pH of the mixture is in the range of about 1 to about 3.

18. The method of claim 16, wherein the temperature of said mixture is less than the boiling point thereof.

19. The method of claim 16, wherein the temperature of said mixture is not greater than about 100° C.

* * * * *